United States Patent [19]
Holt et al.

[11] Patent Number: 5,243,539
[45] Date of Patent: Sep. 7, 1993

[54] METHOD FOR PREDICTING PHYSICAL PARAMETERS IN A DIFFUSION PROCESS

[75] Inventors: Fred B. Holt; David I. Feinstein, both of Seattle, Wash.

[73] Assignee: The Boeing Company, Seattle, Wash.

[21] Appl. No.: 406,761

[22] Filed: Sep. 13, 1989

[51] Int. Cl.$^5$ ............................................. G06F 15/20
[52] U.S. Cl. ..................................... 364/500; 73/232
[58] Field of Search .............. 364/500, 556, 565, 569, 364/148; 73/23, 23.2

[56] References Cited

U.S. PATENT DOCUMENTS 3,069,654 12/1962 Hough ..................................... 382/11
4,882,781 11/1989 Allington ................................ 364/558

Primary Examiner—Jack B. Harvey
Assistant Examiner—Ellis B. Ramirez
Attorney, Agent, or Firm—Christensen, O'Connor, Johnson & Kindness

[57] ABSTRACT

A method for processing data produced by a chemical sensor to predict a rate of diffusion and steady-state level of a chemical vapor absorbed by a coating applied to the chemical sensor. A chemical sensor (10) includes a surface acoustic wave device (12) in which a polymer coating (34) is provided to absorb a chemical vapor. As the vapor is absorbed by the polymer coating, a resonant frequency associated with the SAW device changes in proportion to the mass of the vapor absorbed. The change in resonant frequency is periodically sampled by a high-speed counter (58), digitized, and filtered by a microprocessor (100). In processing the filtered data, the microprocessor describes each data point as a constraint line in a ($\tau$,C) space, where $\tau$ corresponds to the rate of diffusion of the chemical vapor into the polymer and C corresponds to the concentration of the chemical vapor in the polymer at a time t. A minimum energy function $L(\tau,C)$ is determined for successive groups of constraint lines, eventually enabling final values for both $\tau$ and C to be predicted. The predicted values are used to detect and identify the chemical vapor to which the chemical sensor is exposed, well before the concentration of the chemical vapor in the polymer reaches a steady-state level.

12 Claims, 5 Drawing Sheets

METHOD FOR PREDICTING PHYSICAL PARAMETERS IN A DIFFUSION PROCESS

TECHNICAL FIELD

The present invention generally pertains to a method for processing a signal indicative of a physical parameter that is changing in time, and more specifically, relates to a method for estimating both the value of the physical parameter as the process approaches completion and the time required for the physical parameter to reach that value.

BACKGROUND OF THE INVENTION

Complex physical processes are often more easily understood by developing a simplified model to describe the relationship between the variables defining the process. The diffusion of solute into a solvent is such a process. Use of the modeling approach is therefore particularly applicable to a surface acoustic wave (SAW) device in which a chemical vapor is absorbed by a polymeric coating. The polymeric coating applied to a surface of the SAW device is selected to absorb a desired range of chemical vapors. As a chemical vapor diffuses into the polymeric coating, it changes the mass of the coating, and thus correspondingly changes the phase and delay of a Rayleigh surface wave propagating between electrodes disposed at each end of the polymer coated surface. By monitoring the change in resonant frequency of an amplifier connected with the SAW device in its feedback loop, the diffusion of the chemical vapor into the polymer coating and its steady-state level within the coating can be determined. Chemical detectors have been built that comprise an array of SAW devices, each device having a different polymer coating exhibiting a unique characteristic solubility for a specific chemical vapor or class of chemical vapors to which the chemical detector might be exposed. The chemical detector is thus usable to identify a specific chemical substance, based on the relative steady-state levels of the chemical substance in the different polymer coatings of each SAW device in the array.

A simple model for the diffusion of a chemical vapor into the polymer coating of a SAW device has been proposed, corresponding to an ideal one-dimensional diffusion. In the general case, a diffusion process is typically described by the equation:

$$f(t) = C_o - \sum_{n=1}^{\infty} C_n e^{-t/\tau_n} \quad (1)$$

where
- f(t) represents a signal that varies as diffusion proceeds;
- $C_o$ is the steady-state level of the signal f(t);
- $C_n$ are the $C_1 \ldots C_\infty$ components of the diffusion process;
- $\tau_n$ are the reciprocals of the decay times for each of the n components, ordered by magnitude, with $\tau_1$ being the largest: and
- t is the elapsed time for the diffusion.

Applying Equation 1 to a SAW device used as a chemical detector, the value of f(t) defines the resonant frequency of the SAW device at time t. For a given concentration of a chemical substance in the SAW sensor coating, $C_o$ represents the resonant frequency for the steady-state level of that substance within the coating. The summation of the components on the right of Equation 1 defines the transition from an earlier steady-state level to $C_o$, following a change in the ambient concentration of the chemical substance.

Based on the simplified model described by Equation 1, the resonant frequency associated with the SAW device should change exponentially, starting at an initial time, $t_0$, when it is first exposed to a chemical vapor, until at a time, $t_0 + 3\tau_1$, when the frequency is within a few percent of its new steady-state level, $C_o$. Unfortunately, although the experimental data for a diffusion process may visually appear to fit this simple exponential form when graphically illustrated, such data in fact deviate sufficiently from the model and the equation to create problems in predicting the time constant for diffusion, $\tau$, and the steady-state level, C, of the chemical substance in the coating of a SAW device.

The ability to predict the time for diffusion and the steady-state level of a chemical vapor into a polymer coating of a SAW device (represented by its resonant frequency) is particularly important in applications where the SAW device may be used to detect very dilute concentrations of potentially harmful chemical vapors, or alternatively, where the concentration of chemical vapor is so great that it would quickly saturate the SAW device, rendering it unusable for detecting other chemical vapors for an extended period of time. Clearly, the detection and identification of harmful substances must be completed as rapidly as possible, before personnel exposed to the chemical substance are critically affected. Since, for a very dilute ambient concentration of a chemical vapor, it may require up to 15 minutes for the diffusion of the chemical vapor into the polymer coating of a SAW device to asymptotically approach a steady-state level, early prediction of that parameter, e.g., within 3-4 minutes, may correspondingly greatly reduce the time required for identification of a potentially harmful substance. In addition, since various chemical substances are more effectively characterized by both their steady-state level and the time constant for diffusion of the substances into a specific polymer coating, early prediction of the time constant for diffusion is equally important. Use of these two predicted values to identify a chemical substance and to determine its ambient concentration is the subject of a commonly assigned U.S. Pat. No. 4,895,017, entitled, "Apparatus and Method For Early Detection and Identification of Dilute Chemical Vapors," filed Jan. 23, 1989.

The simple exponential model discussed above fails to deal with an initial negative rate of diffusion that is reflected in the resonant frequency data produced by a SAW device exposed to a chemical vapor. In addition, the above model is based on the assumption that the exponential function does not change in time. The actual experimental data developed from SAW devices show that the exponential function varies in time and is not "well behaved" in its initial change when first exposed to a chemical vapor. It is possible to predict the time for diffusion and the asymptote of the diffusion process using a Kalman filter technique, but this approach may not provide optimum speed and accuracy.

Although specifically developed for use with the SAW device, a method for determining a steady-state level and a time to achieve the steady-state level in accordance with the present invention is generally applicable for use with any time-varying exponential process, e.g., to predict the time and final charge on a capacitor as current flows into it through a solid-state switch, or to predict parameters relating to the flow of heat into or out of an object. Complicating any of these time varying exponential processes are the random variations in experimental data from which parameters characterizing the processes must be developed. The problem arises because datum developed experimentally may deviate substantially from the nominal best fit time varying exponential curve. It is therefore relatively difficult to use traditional techniques to fit a time varying exponential curve to such data.

In consideration of the above problems, it is an object of the present invention to provide a method for predicting an asymptote of a signal that changes according to a time varying exponential curve. It is a further object of this invention to predict the characteristic time required for the signal to substantially approach an asymptotic value. Yet a further object is to map preliminary diffusion data into an asymptote/time domain, permitting the data to be fit to a time varying exponential curve, from which the asymptote and time for diffusion may be predicted. These and other objects and advantages of the present invention should be apparent from the attached drawings and the Disclosure of the Preferred Embodiment that follows.

SUMMARY OF THE INVENTION

In a diffusion process wherein a signal indicative of the progression of the process evolves with time such that the signal exponentially approaches a steady-state level at a diffusion rate, a method is provided for predicting both the steady-state level of the signal and the diffusion rate substantially before the diffusion process reaches the steady-state level. The method includes the step of representing values of the signal at corresponding points in time during the diffusion process as a succession of constraint lines in a state space, where the constraint lines are defined by the signal and its rate of change about successive points in time. A preliminary steady-state level and a preliminary diffusion rate are repetitively determined as a point in state space for successive groups of the constraint lines, so as to minimize, for each group, an error that is a function of a distance in the state space between the point associated with the group and each constraint line in the group. The state space comprises all possible pairings of diffusion rate and steady-state level. The rate of change is then determined for either the preliminary steady-state level or the diffusion rate. As a function of the rate of change of either of the preliminary steady-state level or the diffusion level, the predicted steady-state level of the signal and the predicted diffusion rate for the diffusion process are identified.

Each constraint line in the state space is defined by an equation of the form $c = \dot{f}\tau + f$, where c is the preliminary steady-state level, $\dot{f}$ is the rate of change of the signal, $\tau$ is the preliminary diffusion rate, and f is the signal. The distance, d, between a point on the time varying exponential curve and a constraint line can be determined from an equation of the form $d = |\dot{f}\tau + f - c|$.

The preliminary steady-state level is generally defined by a differential equation, $c(t) = \tau(t)df(t)/dt + f(t)$, in which, at time t, f(t) is the signal, c(t) is the steady-state level, and $\tau(t)$ is the reciprocal of the diffusion rate. At each of the points in time during the diffusion process, the value of the signal and its rate of change determine a point in a phase plane defined by f(t) and df(t)/dt. In one preferred form of the method, least-squared distances between N such points and one of the constraint lines at a time t determine each of the constraint lines, and the constraint lines have a slope of $-1/\tau(t)$ and an intercept $c(t)/\tau(t)$. Each group includes N constraint lines, and a next group of constraint lines includes a successive constraint line and the preceding $N-1$ constraint lines in time. The error may include a penalty term that penalizes a successive preliminary diffusion rate in proportion to its difference from a previously determined preliminary diffusion rate.

DESCRIPTION OF THE PREFERRED EMBODIMENT

While the method comprising the present invention has application to other exponential processes, it was specifically developed for use in processing data output from a surface acoustic wave (SAW) chemical vapor detector. The method enables detection and early identification of a chemical vapor by predicting a time constant (or rate) for diffusion and a predicted steady-state level of a chemical vapor as it diffuses into a polymer coating applied to the SAW device, well before the level of the chemical vapor has reached its steady-state in the polymer coating. As noted above, a method and apparatus for early detection and identification of chemical vapors are disclosed in commonly assigned U.S. Pat. No. 4,895,017, entitled "Apparatus and Method For Early Detection and Identification of Dilute Chemical Vapors", filed on Jan. 23, 1989. The present invention provides an alternative method for predicting the time constant for diffusion and steady-state level of a chemical vapor in a SAW sensor that is more accurate than the applied optimal prediction Kalman filter technique discussed in the above-referenced patent application.

Figure 1:
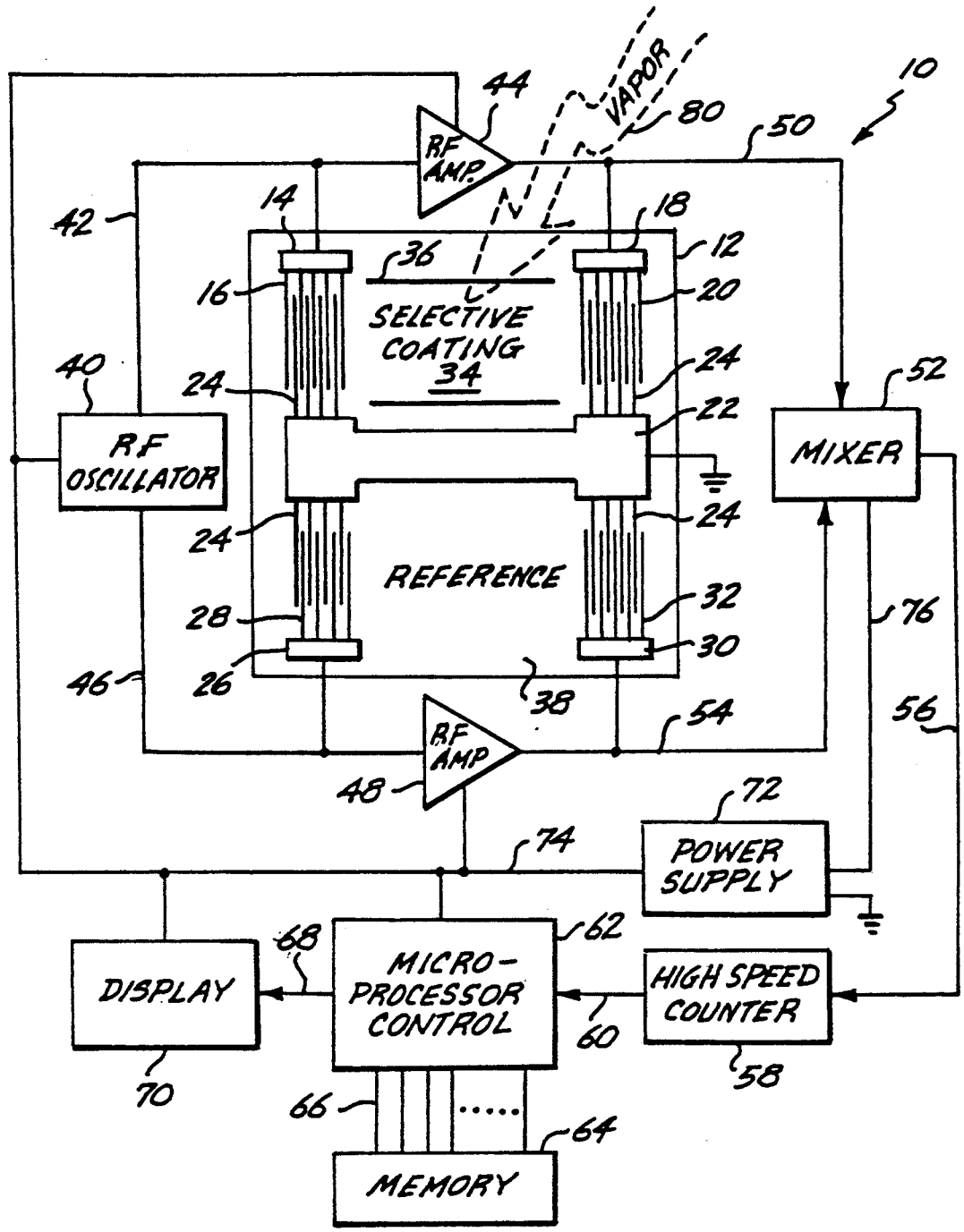
FIG. 1 is a schematic block diagram of a SAW device used in a chemical vapor detector implementing the method of the present invention.

Since the present invention may preferably be used in connection with a SAW chemical sensor, it is helpful to understand the operation of such a sensor. Turning to FIG. 1, a chemical sensor employing a SAW device 12 is generally shown at reference numeral 10. SAW devices are well known to those of ordinary skill in the art; however, operation of a SAW device as a chemical sensor will be briefly described. SAW device 12 comprises a piezoelectric substrate that functions as a mechanically resonant structure through which Rayleigh surface waves propagate. Electrodes 14 and 18 are disposed adjacent a common edge of SAW device 12, at opposite ends of the substrate. Extending from electrode 18 are a plurality of interdigital electrodes 20. A common ground electrode 22 is disposed along the longitudinal center of SAW device 12, and is connected to circuit ground. A plurality of interdigital electrodes 24 extend outwardly from each end of electrode 22 in alternating relationship with both interdigital electrodes 20 and with a plurality of interdigital electrodes 16 extending from electrode 14.

Along the opposite edge of SAW device 12 are disposed an electrode 26 and an electrode 30, corresponding respectively to electrodes 14 and 18. A plurality of interdigital electrodes 28 and 32 extend respectively from electrodes 26 and 30 toward electrode 22 in alternating relationship with interdigital electrodes 24. A region 36 is disposed in the center of the substrate, between interdigital electrodes 20 and 26, and comprises a coating of a polymer selected for its characteristic affinity to absorb a group of related chemical substances. Examples of such polymers include polyethylene maleate, fluoropolyol, collodion, abietic acid, polyacrylic acid, polystyrene, polyvinyl pyrollidone, polyethylene imine, polyethylene adipate, polychloroprene, chlorinated rubber, carbowax 20M, polyisobutylene, polycaprolactone, polyepichlorohydrin, ethylcellulose, polyhydroxypropyl methacrylate, and other polymers known to absorb specific chemical substances. A corresponding area 38 between interdigital electrodes 28 and 32 is either not coated, or is coated with a vapor-impermeable material that does not absorb any chemical substance of interest.

In addition to SAW device 12, chemical sensor 10 includes an RF oscillator 40, which is connected through a lead 42 both to electrode 14 and to an input of an RF amplifier 44. The same RF signal produced by RF oscillator 40 is also connected through a lead 46 to electrode 26 and to an input of an RF amplifier 48. The output of RF amplifier 44 is connected through a lead 50 to electrode 18 and to one of two inputs of mixer 52. In a similar manner, the output of RF amplifier 48 is connected through a lead 54 to electrode 30 and to the other input of mixer 52. An output from mixer 52 is connected through a lead 56 to an input of a high-speed counter 58. High-speed counter 58 produces a digital signal, indicative of a beat or difference frequency of the signals input to mixer 52, which is conveyed through a lead 60 to the input of a microprocessor control 62. Microprocessor control 62 processes the digital signal produced by high-speed counter 58 according to the method of the present invention, following programmed steps that are stored in an electronic memory 64. Address/data lines 66 convey data bidirectionally between microprocessor control 62 and electronic memory 64, permitting the microprocessor control to access the program stored in the electronic memory and to temporarily store variables within the electronic memory for later access.

A lead 68 connects the microprocessor control to a display 70, so that a detected chemical substance of interest and its relative ambient concentration can be identified and read by an operator of the sensor. The detection and identification of the substance do not comprise a significant part of the present method, but instead, depend upon the practice of the present invention, since the chemical vapor is detected and identified based upon values for a predicted rate of diffusion and a predicted steady-state level of the chemical vapor in the selective coating 34, as determined by the method.

Each of the active components of chemical sensor 10 is energized by a power supply 72 through leads 74 and 76. The power supply and other components of the circuitry shown in FIG. 1 are of a generally conventional design, well known to those of ordinary skill in the art.

RF oscillator 40 produces a radio frequency sinusoidal voltage that is applied simultaneously to both electrodes 14 and 26, generating Rayleigh waves that travel across the surface of SAW device 12 toward the interdigital electrodes disposed at the opposite end. Since most of the energy of the Rayleigh waves is constrained to be at the surface of the SAW device, these waves interact with any material that is in contact with the surface, such as the selective coating 34 applied in region 36 between interdigital electrodes 16 and 20. As the mass of selective coating 34 changes due to absorption of a chemical vapor, represented by arrow 80 in FIG. 1, the mechanical modulus of the surface is altered and the velocity of the Rayleigh waves changes proportionally. Changes in the Rayleigh wave velocity appear as shifts in the resonant frequency of the surface acoustic wave propagating between interdigital electrodes 16 and 20.

Since regions 36 and 38 are formed on a common piezoelectric substrate in SAW device 12, drift in the resonant frequency of the selectively coated portion of the SAW device due to changes in ambient temperature and pressure is readily compensated. Comparison of the resonant frequency of the reference half (region 38) and the selectively coated half (region 36) of the piezoelectric substrate is accomplished by mixing their resonant frequencies in mixer 52. The output of mixer 52 thus represents a beat frequency proportional to the difference between the surface acoustic wave transmitted through the selective coating and that transmitted through the reference portion of the device. The pulses output from mixer 52 are counted by high-speed counter 58, and the resultant count is periodically monitored by microprocessor 62. This count comprises the signal representative of the diffusion of chemical vapor into selective coating 34. The present invention predicts the rate of diffusion of the chemical vapor and its steady-state level in the selective coating in region 34 based on the count, well before the steady-state level is achieved.

The only physical parameter used in prior art SAW chemical sensors to identify chemical substances has been the steady-state level of the chemical substance absorbed into a polymer coating on one or more SAW devices, determined by monitoring the change in resonant frequency of the surface acoustic wave transmitted through the polymer coating, after it has stabilized following a step change in the ambient concentration of the chemical substance. However, the present method provides a technique for predicting both the steady-state level and a second parameter, the time for diffusion (rate at which the chemical substance absorbed by the selected polymer approaches its steady-state level). Moreover, it treats these parameters not as constants, but as variables over time.

Figure 2:
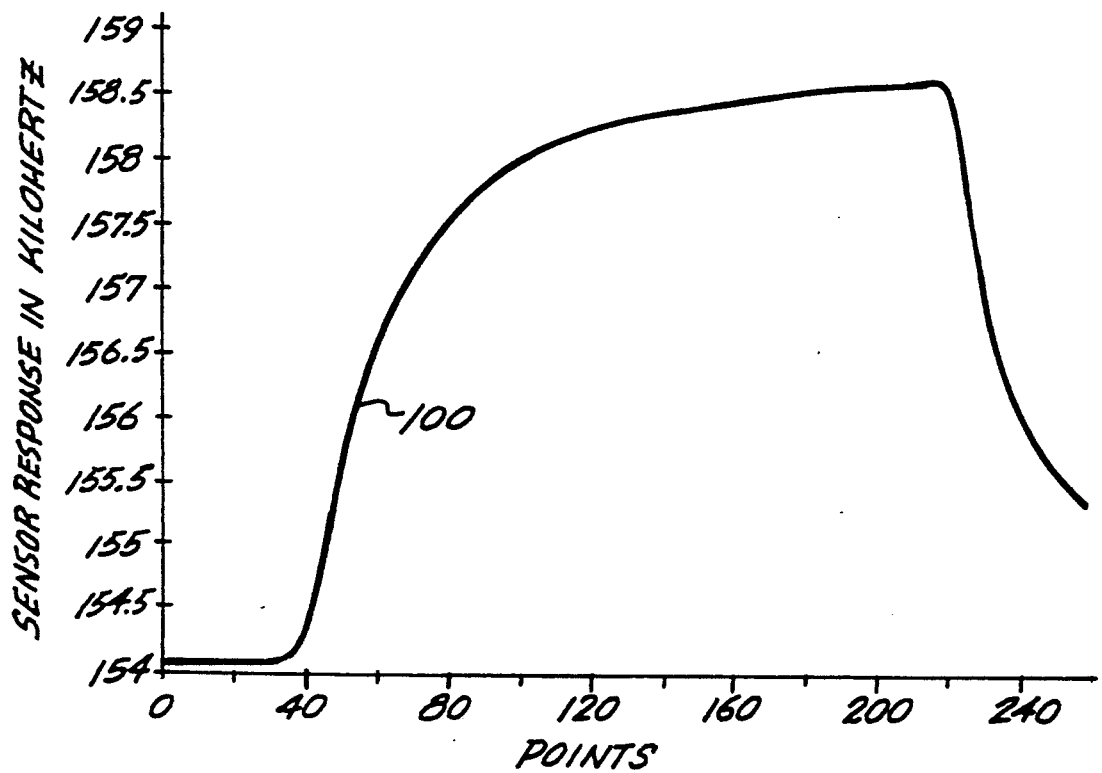
FIG. 2 is a graph showing filtered data that indicate changes in the resonant frequency of a SAW device as methyl salicylate vapor diffuses into a polymer coating on the device, while successive samples are taken (i.e., as a function of time)

Turning now to FIG. 2, a curve 100 illustrates filtered data representing the resonant frequency of a SAW device having a fluoropolyol polymer coating, as the SAW device is exposed to a relatively low ambient air concentration of methyl salicylate vapor. Curve 116 is an exponential curve that changes in time as the methyl salicylate vapor is absorbed into the fluoropolyol polymer on the SAW device. The increase in mass of the polymer coating due to the absorption of the methyl salicylate vapor causes an exponential change in the difference or beat frequency of the SAW device, from an initial value of 154.1 kilohertz, to a steady-state value of approximately 158.6 kilohertz. In this test, approximately 220 data points were sampled before the flow of methyl salicylate vapor into the SAW device was terminated; the mass of the methyl salicylate within the polymer coating thereafter decreased by desorption.

Curve 100 in FIG. 2 is not a pure exponential function. For example, as the SAW device is initially exposed to the methyl salicylate vapor, curve 100 follows an inverse exponential curve from its initial value at 154.1 kilohertz, but then gradually changes over to the time-varying exponential function that it follows until it reaches its asymptotic value.

The simplest differential model for diffusion assumes only that the quantity of chemical vapor that diffuses into the polymer coating on a SAW substrate is proportional to time, t, and to the difference between the ambient concentration and the instantaneous concentration of the vapor in the polymer coating, represented by the resonant frequency signal f(t). The differential equation that defines this relationship is:

$$\tau(t)\frac{df}{dt} = C(t) - f(t) \quad (2)$$

where $\tau(t)$ is the constant of proportionality, i.e., the reciprocal of the diffusion rate at time t, and C(t) is the asymptotic value of the frequency at a steady-state level of the vapor in the SAW sensor at time t. Equation 2 is linear in $\tau$ and C, and therefore, at any given instant of time, Equation 2 constrains $\tau$ and C to lie on the line $C = \dot{f}\tau + f$. A plane or state space comprising all possible pairs of $\tau$ and C contains lines having the slope $\dot{f}$ and a C axis intercept f. With each successive sample of the signal, f, and its time derivative, $\dot{f}$, $\tau$ and C are constrained to fall on a new line in the ($\tau$,C) plane. If during the diffusion process, $\tau$ and C were truly constant, all of the constraint lines developed from the preceding equation for line C would intersect at a single point ($\tau$,C). However, $\tau$ and C evolve with time so that the point of intersection of successive lines traces a trajectory in the ($\tau$,C) plane or state space. In fact, the locus of intersections of successive constraint lines forms an envelope that defines a trajectory of the developing parameters for $\tau$ and C over time.

Mathematicians will readily appreciate that the time history of the signal described by Equation 2 does not inherently specify unique solutions for two unknown functions $\tau(t)$ and C(t). Based solely upon Equation 2, it would appear that there are an infinite number of $\tau(t)$ and C(t) pairs that are compatible with a given f(t). However, the constraint envelope is determined by another property of the model that applies to the ($\tau$,C) state space—that $\tau(t)$ and C(t) are chosen to maximize the continuity measures defined by $-\int(d\tau/dt)^2 dt$ and $-\int(dC/dt)^2 dt$.

The signal produced by the SAW device as the chemical vapor is absorbed into the polymer coating is not noise free, even though microprocessor control 62 provides digital filtering of the signal to minimize the effects of random variations in the difference frequency. The approach used to deal with the presence of noise in the successive samples of the differential (or beat frequency) count produced by high-speed counter 58 is to characterize the envelope of constraint lines as the minimum of an energy function. This characterization permits a modified least-squared technique to be used to find a minimum at any given time, t.

Since real data output from SAW device 12 are too noisy to determine predicted values for $\tau$ and C simply as successive intersections of constraint lines in the ($\tau$,C) space, a series of points in the ($\tau$C) space are determined for successive predicted values of $\tau$ and C, where each point is selected to lie as close as possible to a weighted collection of N constraint lines. Each such point minimizes the equation:

$$L(\tau,C) = \sum_{i=1}^{N} W_i(C - \dot{f}_i\tau - f_i)^2 + \lambda(\tau - \tau_0)^2 \quad (3)$$

wherein the term $\lambda$ is an experimentally determined correction factor that encourages continuity in the predicted values for $\tau$. It will be understood that a correction factor $\lambda'$, in terms of $(C-C_0)$ could alternatively be applied. For simplicity, the parameter $\lambda$ or ($\lambda'$) may be initially set to zero. The resulting energy function $L(\tau,C)$ is then reduced to the sum of squared distances, where each ith term in the sum is a measure of the squared vertical (or horizontal) distance from the point ($\tau$,C) to the ith constraint line. So long as either the vertical or horizontal distance is consistently used, the result is the same. Alternately, if a denominator, $(1 + \dot{f}_i^2)$, is inserted under the summation of $(C - \dot{f}\tau - f_i)^2$, the result is simply the least-squared distance between each point and one of the constraint lines. This distance can also be used to determine $L(\tau,C)$. For the ideal case where all of the constraint lines intersect at a single point, the value of $L(\tau,C)$ is zero at that point. However, using real data, all the lines do not intersect at a single point. Each of the $W_i$ are positive weighting factors that determine the importance of each constraint line's agreement with each of the ($\tau$,C) points. With respect to the ($\tau$,C) plane, the energy function $L(\tau,C)$ has a single minimum. Accordingly, the partial derivatives of L can be set equal to zero in order to locate the $\tau$ and C coordinates of the energy function minimum. The $\tau$ and C coordinates are defined by the following vector relationships:

$$\begin{bmatrix} \tau \\ C \end{bmatrix} = (A + B)^{-1}\vec{r} \quad (4)$$

$$\text{where } A = \sum_{i=1}^{N} \frac{W_i}{1 + \dot{f}_i^2} \begin{vmatrix} -\dot{f}_i & 1 \\ \dot{f}_i^2 & -\dot{f}_i \end{vmatrix};$$

$$B = \lambda \begin{vmatrix} 0 & 0 \\ 1 & 0 \end{vmatrix};$$

$$\text{and } \vec{r} = \sum_{i=1}^{N} \frac{W_i}{1 + \dot{f}_i^2} \begin{vmatrix} f_i \\ -\dot{f}_i f_i \end{vmatrix} + \lambda \begin{vmatrix} 0 \\ \tau_0 \end{vmatrix}.$$

The term with $\lambda$ encourages continuity in the data, where $\tau$ has changed significantly from its previous value. The term $\lambda(\tau - \tau_0)^2$ in Equation 3 is a penalty term that penalizes each successive value for $\tau$ in proportion to its difference from an immediately previous value of $\tau$. This term deforms the energy surface $L(\tau,C)$, by pulling the location of the minimum toward the previous value of $\tau$. The magnitude of $\lambda$, controls the relative strength of the penalty term. When $\lambda$ is equal to zero, there is no provision encouraging continuity for $\tau$, but as $\lambda$ increases in a positive direction, the importance of the penalty term grows with respect to the importance of the constraint lines. In the preferred embodiment, a value for $\lambda$ is selected that is relatively close to zero, e.g. 0.0005, but the value used for $\lambda$ is not particularly critical. It is possible to refine the present method to select $\lambda$ during the process of predicting $\tau$ and C, i.e., on the fly, guided by the mathematical structure of Equation 4 so as to bound the condition number of $(A+B)$. The condition number of a matrix, K, is the absolute value of the ratio of the largest to smallest eigenvalue. This dimensionless ratio approaches infinity as the matrix approaches singularity.

As the constraint lines become nearly parallel, intersecting one another along an extended region parallel to the $\tau$ axis, continuity in the selection of a $\tau$ coordinate is important in determining which point in the extended region is the optimum choice for $\tau$ and C. When the constraint lines are more nearly vertical, continuity in the selection of $\tau$ is less important.

Figure 3:
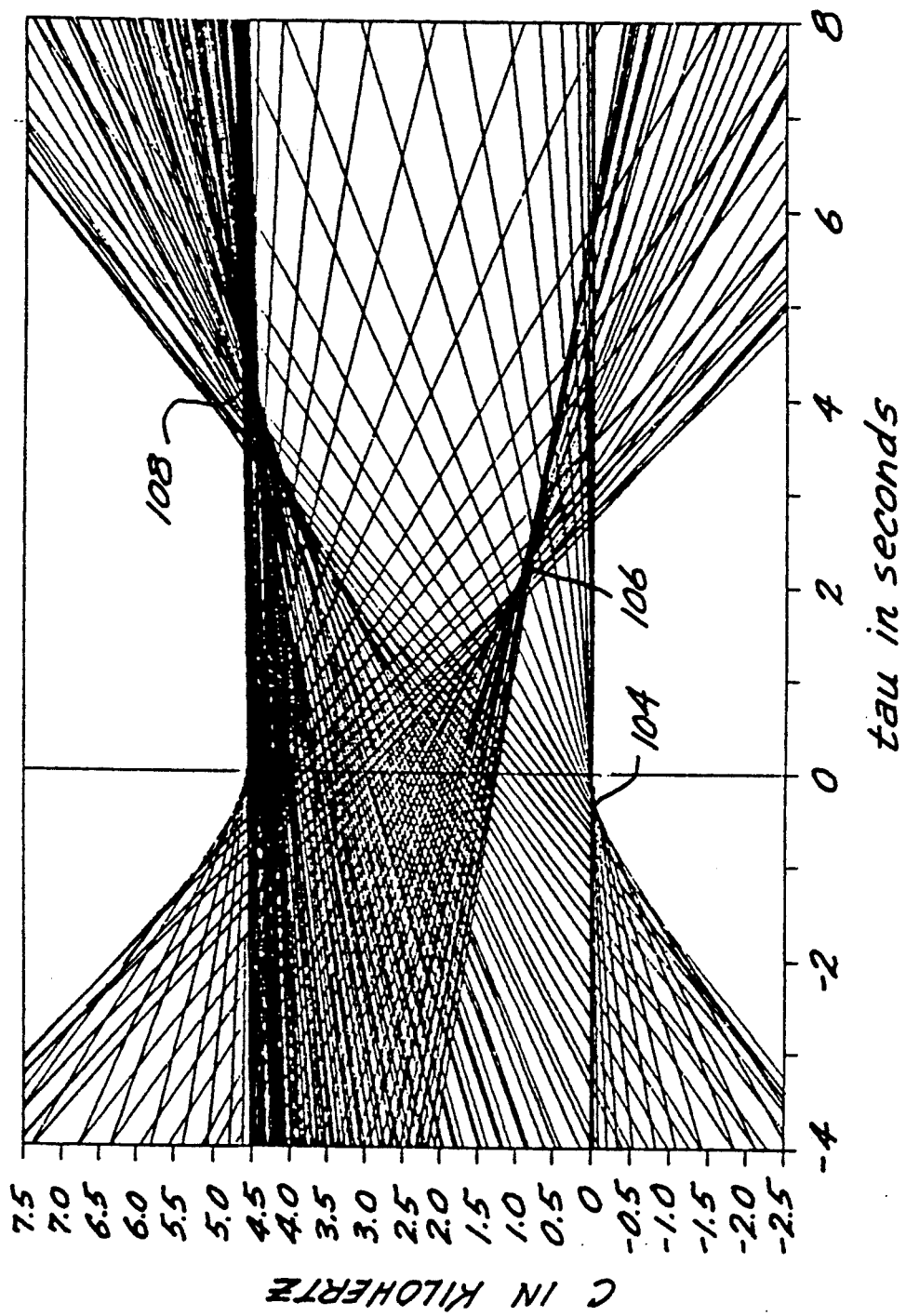
FIG. 3 is a graph showing constraint lines plotted for the data of FIG. 2.

Turning now to FIG. 3, constraint lines corresponding to the data shown in FIG. 2 are plotted in the $(\tau,C)$ plane. By inspection of FIG. 3, it is possible to visually select approximate values for each of three predicted points for $\tau$ and C corresponding to different portions of curve 100 in FIG. 2. For example, a plurality of constraint lines intersect at or near a point indicated by reference numeral 104, which defines a minimum (zero) concentration of methyl salicylate in the sensor, i.e., the condition that exists during approximately the first 30 sample points. Similarly, a plurality of constraint lines converge at a point 106 where $\tau$ is approximately equal to 2.2 and C is approximately equal to 0.9 kilohertz, corresponding to an asymptotic value for the inverse exponential portion of the curve that occurs after about 4 sample points have been taken. Neither points 104 nor 106 are of much interest, since they do not define an asymptotic value for C with respect to the steady-state absorption of the chemical vapor within the polymer coating of the SAW device. The intersection of a majority of the constraint lines at a point 108 defines this final steady-state level of the vapor. It is apparent that for point 108, the value of C is approximately 4.5 kilohertz, and the value of $\tau$ is approximately four seconds. By inspection of FIG. 2, it can be seen that the difference between the sensor response prior to its exposure to the methyl salicylate vapor (frequency equals 154.1 kilohertz) and its asymptotic value as the vapor reaches steady-state level in the polymer coating in the SAW device is approximately 4.5 kilohertz.

The sampling frequency is approximately 9.6 hertz, i.e., 9.6 samples per second, for the data shown in FIG. 2. The rate of diffusion is defined as the time required for the vapor concentration in the polymer to reach 0.707 of its final steady-state value. Comparing FIG. 5 to FIG. 2, the value of $\tau$ represented by curve 120 (or time for the frequency data of curve 100 to reach 0.707 of its final asymptotic value) occurs after approximately 40 points, which is equal to approximately 4 seconds, in close agreement with the $\tau$ value for point 108 in FIG. 3.

Figure 4:
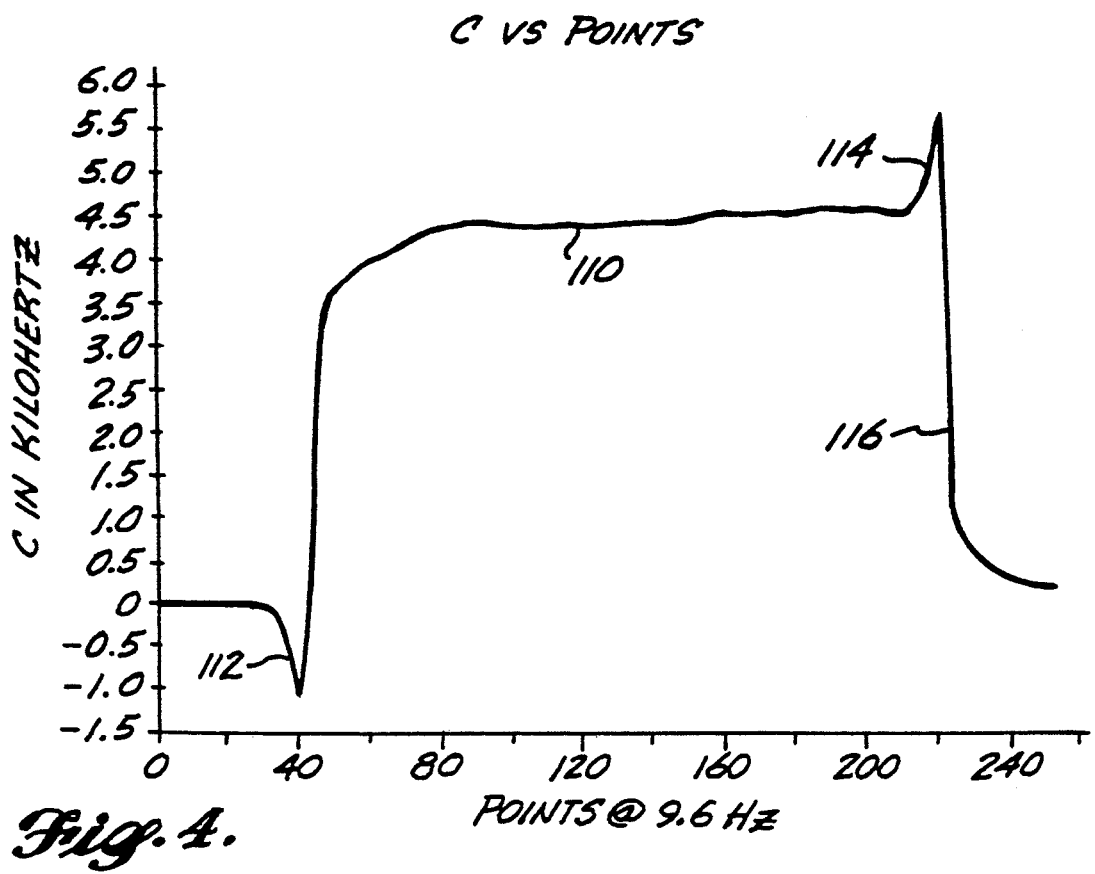
FIG. 4 is a graph showing the predicted steady-state level of methyl salicylate within the polymer coating of the SAW device for the data of FIG. 2.
Figure 5:
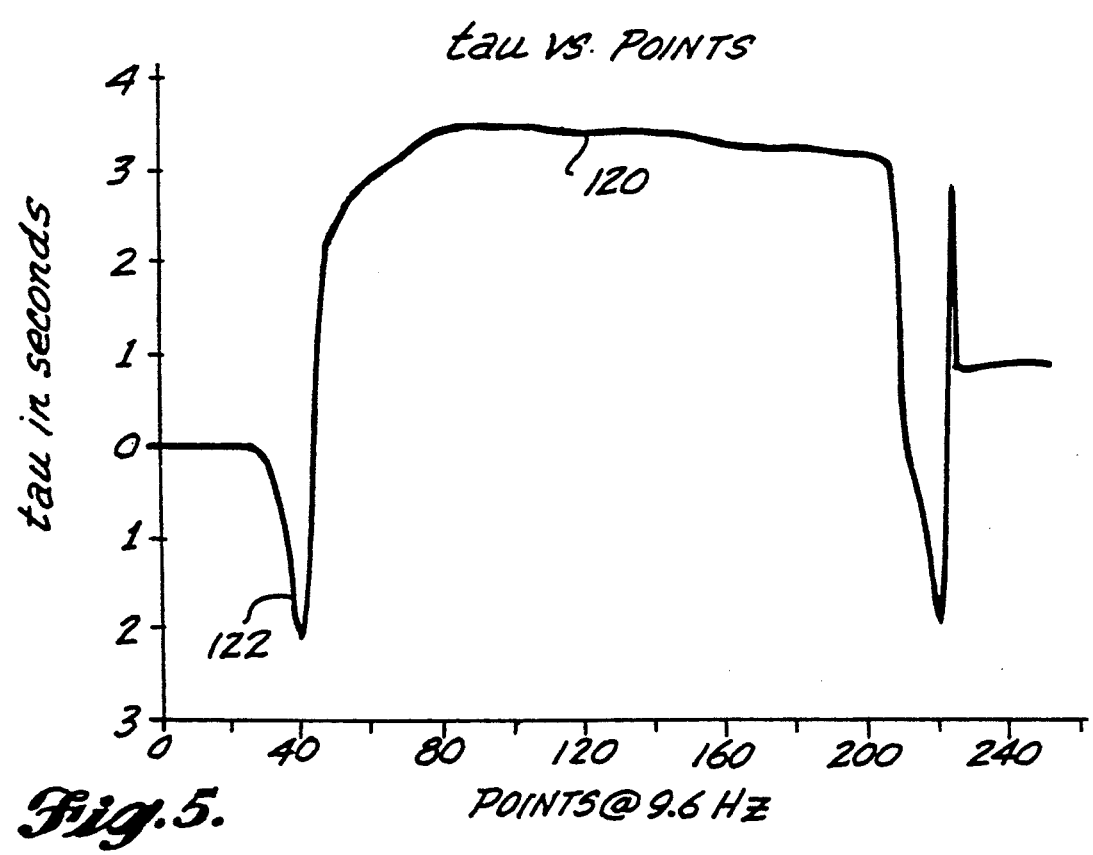
FIG. 5 is a graph showing the predicted time constant for the diffusion of methyl salicylate within the SAW device, for the data of FIG. 2.

In FIGS. 4 and 5, predicted values for C and $\tau$ are respectively presented as a function of successive data samples or points corresponding to the sensor frequency data of FIG. 2. In FIG. 4, the predicted value of C is plotted with respect to the number of points sampled. Negative values for C, indicated for example, at a reference numeral 112, correspond to the inverse exponential portion of curve 100 in FIG. 2. The final predicted value for C is obtained with only a few percent error in approximately 40 data samples after the SAW device is first exposed to the methyl salicylate vapor. Similarly, in FIG. 5, a relatively accurate prediction of $\tau$ is achieved within approximately 40 data samples after exposure of the SAW device to the vapor.

The predicted value for $\tau$ shown in FIG. 5 is similarly robust, providing significant confirmation that the predicted values for both C and $\tau$ correspond to good estimates of the actual or empirical values for these parameters. At reference numeral 114 in FIG. 4, a portion of the curve sharply increases as the exposure of the SAW device to methyl salicylate vapor is terminated, perhaps due to a step change response in the data. Further, it is interesting to note that at a reference numeral 116, the curve in FIG. 4 drops abruptly, corresponding to the inverse exponential desorption of methyl salicylate from the polymer in the SAW device.

Selection of a final predicted value for $\tau$ and C may be based upon the rate of change of either or both parameters. For example, if the rate of change of either predicted parameter is approximately zero for a predetermined number of data samples following a positive change, the values likely represent good final predicted values for the parameters at steady-state. Clearly, with respect to either a level portion 110 of the curve in FIG. 4 or a level portion 120 of the curve in FIG. 5, the method provides for determination of the final predicted value well before the concentration of the chemical vapor absorbed into the polymer of SAW device 10 reaches steady-state.

Figure 6:
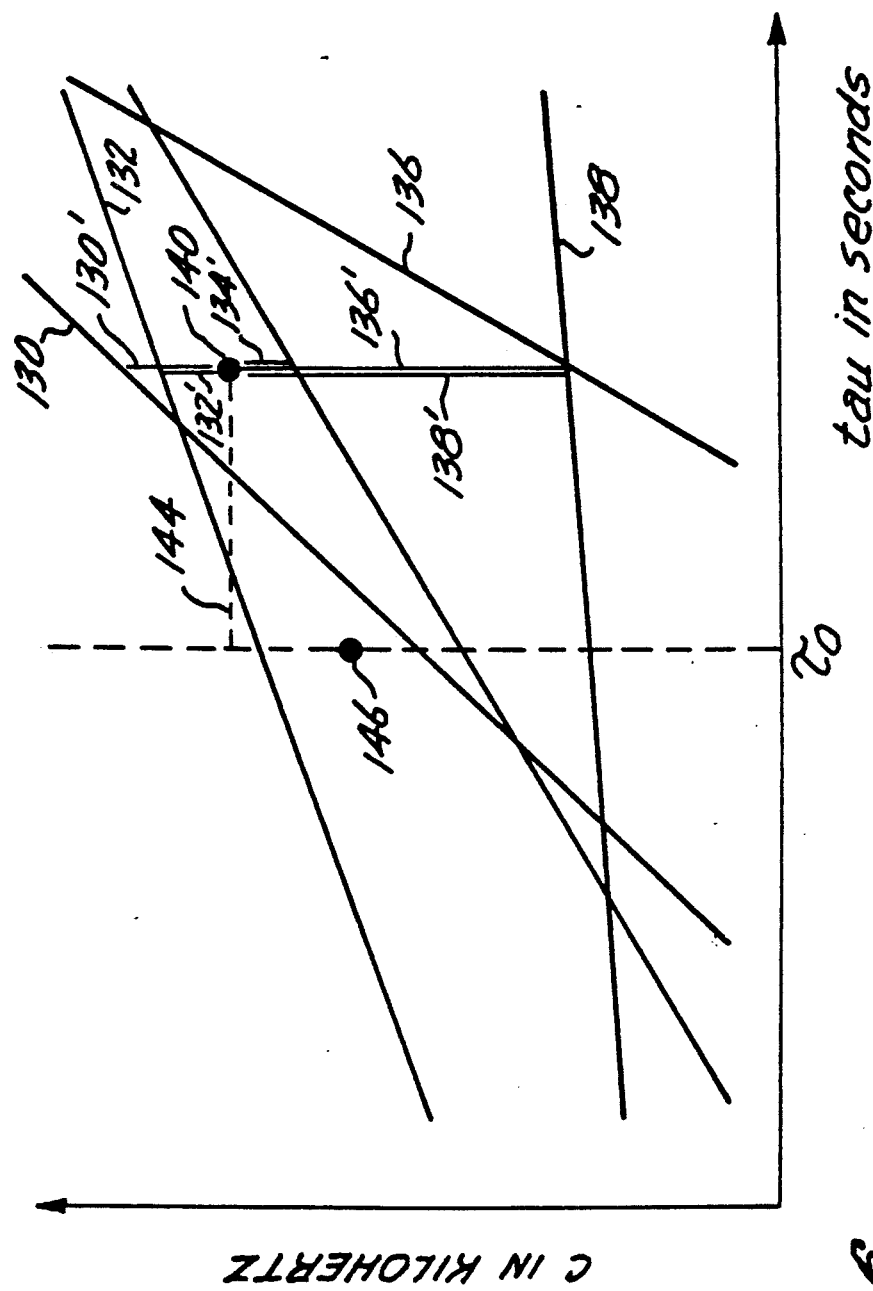
FIG. 6 graphically illustrates how a group of constraint lines defines a point that best describes an exponential process.

In FIG. 6, a plurality of constraint lines 130, 132, 134, 136, and 138 are developed by applying Equation 4 to five successive samples of filtered data. As explained, the data is filtered to minimize the effects of random variations in the resonant frequency output from the SAW device as the chemical vapor is absorbed into the polymer coating. It will be apparent that Equation 2 is generally equivalent to the well known equation for a line, $y=mx+b$, where y equals $C(t)$, i.e., the independent variable for C in the $(\tau,C)$ plane; m equals $df/dt$, or rate of change of SAW device 10, which is determined simply by dividing the difference in frequency between two successive samples by the time between the samples; x equals $\tau$, which has dimensions of time, i.e., the time between each sample; and b equals $f(t)$, the frequency at time t, i.e., the output frequency from SAW device 10. Thus, five constraint lines 130–138 illustrated in FIG. 6 are determined in a straightforward manner using simple algebra from five successive data samples filtered by microprocessor 100.

Constraint lines 130–138 do not intersect in a common point. Therefore, the next step in reducing the data is to determine a point 140 having coordinates in the $(\tau,C)$ plane that corresponds to the minimum of the energy function $L(\tau,C)$. Equation 4 is applied to determine the coordinates of point 140 which is a point that lies closest to the weighted collection of constraint lines 130–138. As shown in FIG. 6, the vertical distances 130'–138' between point 140 and each corresponding constraint line are determined. (Alternatively, the horizontal distance between a point and each of the constraint lines, or the orthogonal projection from each line to a point may also be used to determine the coordinates of point 140, with substantially equivalent results.) Regardless of whether the distance between the point and each constraint is measured in terms of its orthogonal projection on the line, or in terms of the distance between the point and the constraint line measured along a line parallel to either of the two axes defining ($\tau$,C) space, a point 140 can readily be found that represents a minimum energy function for L($\tau$,C). The next step in the method provides for determining the coordinates for a successive point in the ($\tau$,C) space using constraint lines 132-138 (constraint line 130 is no longer used) and a fifth successive constraint line (not shown). By using successive groups of five constraint lines to determine the coordinates $\tau$ and C of each point, the data shown in FIGS. 4 and 5 are developed, permitting relatively robust values for the final predicted values of $\tau$ and C at steady-state to be determined.

The penalty term, $\lambda$, in Equations 3 and 4 represents a correction for a distance indicated at reference numeral 144 in FIG. 6, measured between point 140 and a line extending parallel to the C axis through a point 146. Point 146 is the point determined immediately preceding the present point 140, based on the minimum energy function, L($\tau$,C). The penalty term associated with $\lambda$ has little impact unless the distance 144 is significant. As noted above, $\lambda$ encourages continuity in the value of $\tau$, reducing wide variations in the value as the chemical absorption process approaches steady-state. Alternatively, the penalty term may be associated with the distance between point 140 and a line through point 146 that is parallel to the $\tau$ axis, using $\lambda'$.

Microprocessor 100 is programmed to digitally filter the data input from high-speed counter 58 by applying a Hanning function to the data to reduce widely random variations in the resonant frequency signal. Alternatively, other digital (or analog) filters could be used for this purpose, incorporating parameters selected to optimize particular characteristics of the data being sampled.

Post filtering of the predicted values for $\tau$ and C represents a further evolution of this technique that serves to enhance the speed at which a robust prediction of the final values of $\tau$ and C may be obtained. For example, optimal Kalman filtering may be applied to the predicted values for $\tau$ and C to improve the quality of the final predicted values.

An alternative approach for predicting final values for $\tau$ and C can be implemented by developing a series of data points in an (f(t), df/dt) phase plane from the beat frequency samples, based on Equation 2. Each sample of the beat frequency signal determines a point in the phase plane. In the ideal case, N such points determine a least-squared error line, with slope $-1/\tau$ and intercept $C/\tau$, determining the current predicted value for $\tau$ and C. Noise or other source of random variation in the data produces N points for which a least-squared error can determine a best-fit straight line. As successive groups of N data samples are used, the slope and intercept of the best-fit lines should approach a constant, enabling a final predicted value for both C and $\tau$ to be determined.

While the present invention has been disclosed with respect to a preferred embodiment and modifications thereto, those of ordinary skill in the art will appreciate that further modifications may be made within the scope of the claims that follow. Accordingly, it is not intended that the scope of the invention be in any way limited by the disclosure, but that it be determined entirely by reference to the claims.

The embodiments of the invention in which an exclusive property or privilege is claimed are defined as follows:

1. In a diffusion process that evolves with time such that the diffusion of one substance into another substance exponentially approaches a steady-state level at a diffusion rate, a method for predicting both the steady-state level and the diffusion rate substantially before the diffusion process reaches the steady-state level so as to rapidly identify one of the substances, comprising the steps of:

(a) producing a signal indicative of the progression of the diffusion process;

(b) representing values of the signal at corresponding points in the time during the diffusion process as a succession of constraint lines in a state space, where the constraint lines are defined by the signal and its rate of change about successive points in time;

(c) repetitively determining a preliminary steady-state level and preliminary diffusion rate as a point in the state space for successive groups of the constraint lines so as to minimize, for each group, an error that is a function of a distance in the state space between the point and each constraint line in the group, where the state space comprises all possible pairings of diffusion rate and steady-state level;

(d) determining the rate of change of at least one of the preliminary steady-state level and the diffusion rate;

(e) identifying a predicted steady-state level of the signal and a predicted diffusion rate for the diffusion process as a function of the rate of change of said one of the preliminary steady-state level and the diffusion rate; and (f) based upon at least one of the predicted steady-state level and the predicted diffusion rate, rapidly identifying at least one of the substances substantially before the steady-state level is attained.

2. The method of claim 1, wherein said constraint line in the state space is defined by an equation of the form:

$$C = \dot{f}\tau + f$$

where:
C is the preliminary steady-state level;
$\dot{f}$ is the rate of change of the signal;
$\tau$ is the preliminary diffusion rate; and
f is the signal.

3. The method of claim 2, wherein the error is the square of the distance, d, between a point in the state space and a constraint line, as defined by an equation of the form:

$$d = |\dot{f}\tau + f - c|.$$

4. The method of claim 1, wherein the preliminary steady-state level is generally defined by a differential equation:

$$C(t) = \tau(t)\frac{df(t)}{dt} + f(t)$$

in which, at a time t:
f(t) is the signal;

C(t) is the steady-state level; and

τ(t) is the reciprocal of the diffusion rate.

5. The method of claim 4, wherein at each of the points in time during the diffusion process, the value of the signal and its rate of change determine a point in a phase plane defined by f(t) and df(t)/dt, and wherein least-squared distances between N such points and one of the constraint lines at a time t determine each of the constraint lines, said constraint lines having a slope of $-1/\tau(t)$ and an intercept $c(t)/\tau(t)$.

6. The method of claim 1, wherein there are N constraint lines in each group, the next group of constraint lines including a successive constraint line and the preceding $N-1$ constraint lines in time.

7. The method of claim 1, wherein the error includes a penalty term that penalizes a successive preliminary diffusion rate in proportion to its difference from a previous preliminary diffusion rate.

8. The method of claim 1, wherein said step of identifying includes the step of determining that the rate of change of said one of the preliminary steady-state level and diffusion rate is less than a predetermined value.

9. A method for detecting and identifying a chemical substance from its effect on a surface acoustic wave device, comprising the steps of:
  (a) producing a signal using the surface acoustic wave device that is indicative of a parameter, which changes due to an increase in mass of a material coating on the surface acoustic wave device caused by diffusion of the chemical substance into the material coating, said change in the parameter generally being defined by an exponential curve;
  (b) filtering the signal to minimize effects of a random variation in the parameter, producing filtered data;
  (c) mapping the filtered data into a two-dimensional space defined by the steady state level and the diffusion rate, as a plurality of constraint lines that are defined by a linear relationship between the rate of change of the parameter during a finite interval of time, the diffusion rate, the resonant frequency and the steady-state level of the chemical substance of the material coating at the time each datum was monitored;
  (d) using the constraint lines in the two-dimensional space to determine coefficients of an equation defining the parameter by repetitively determining a plurality of points in the two-dimensional space so as to minimize an error based on distances between successive groups of the constraint lines and the points;
  (e) determining predicted values for the steady-state level and diffusion rate of the chemical substance in the material coating, based on the coefficients of the time varying equation; and
  (f) identifying the chemical substance from among a plurality of chemical substances having predefined characteristic steady-state and diffusion rate values as a function of the predicted values of the steady-state level and diffusion rate.

10. The method of claim 9, wherein the step of mapping comprises the steps of:
  (a) determining the rate of change of the filtered data over the finite interval of time; and
  (b) defining each constraint line by an equation having the form of:

$$C = \dot{f}\tau + f$$

wherein;
  C is the steady-state level of the chemical substance in the material coating during the finite interval of time;
  $\dot{f}$ is the rate of change of the parameter during the finite interval of time;
  τ is the diffusion rate during the finite interval of time; and
  f is a value of the parameter during the finite interval of time.

11. The method of claim 10, wherein the error is defined by the square of a distance between one of the constraint lines and one of the points in the two-dimensional space measured in a direction aligned with an axis defining the two-dimensional space.

12. The method of claim 9, wherein the step of determining coefficients includes the step of minimizing the affect of relatively large random variations in the diffusion rates by including a penalty term with the error, said penalty term having a magnitude that is a function of the difference between values of one of the diffusion rates and the steady-state levels for successive points determined in the state space.

* * * * *

UNITED STATES PATENT AND TRADEMARK OFFICE
CERTIFICATE OF CORRECTION

PATENT NO. : 5,243,539
DATED : September 7, 1993
INVENTOR(S) : F. B. Holt et al.

It is certified that error appears in the above-identified patent and that said Letters Patent is hereby corrected as shown below:

| COLUMN | LINE | |
|---|---|---|
| 3 | 57 | "f" should read $--\dot{f}--$ |
| 7 | 38 | "f" should read $--\dot{f}--$ |
| 8 | 31 | "$(C-f\tau-f_i)^2$" should read $--(C-\dot{f}\tau-f_i)^2--$ |
| 8 (Equation 4) | 60 | "$\dfrac{Wi}{1+f_i^2}$" should read $--\dfrac{Wi}{1+\dot{f}_i^2}--$ |
| 9 | 40 | "4" should read --40-- |
| 12 (Claim 1 | 17 12) | delete "the" (first occurrence) |
| 13 (Claim 9 | 36 Line 14) | "steady state" should read --steady-state-- |

Signed and Sealed this

Tenth Day of May, 1994

*Attest:*

BRUCE LEHMAN

*Attesting Officer*   *Commissioner of Patents and Trademarks*